United States Patent
Gonzalez Vidal et al.

(10) Patent No.: US 10,005,709 B2
(45) Date of Patent: Jun. 26, 2018

(54) METHOD FOR PRODUCING A BISPHENOL

(71) Applicant: SABIC GLOBAL TECHNOLOGIES B.V., Bergen op Zoom (NL)

(72) Inventors: Nathalie Gonzalez Vidal, Bergen op Zoom (NL); Alexander van Goudswaard, Goes (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days. days.

(21) Appl. No.: 15/586,494

(22) Filed: May 4, 2017

(65) Prior Publication Data
US 2017/0327447 A1 Nov. 16, 2017

(30) Foreign Application Priority Data
May 10, 2016 (EP) ..................... 16168830

(51) Int. Cl.
*C07C 37/20* (2006.01)
*B01J 31/10* (2006.01)
*B01J 39/20* (2006.01)
*C08J 3/24* (2006.01)
*B01J 31/00* (2006.01)

(52) U.S. Cl.
CPC ............. *C07C 37/20* (2013.01); *B01J 31/00* (2013.01); *B01J 31/10* (2013.01); *B01J 39/20* (2013.01); *C08J 3/24* (2013.01); *B01J 2231/49* (2013.01); *B01J 2531/004* (2013.01); *C08J 2325/06* (2013.01)

(58) Field of Classification Search
CPC ......... C07C 37/20; C08J 3/24; C08J 2325/06; B01J 31/10; B01J 39/20; B01J 2531/49; B01J 2531/004
See application file for complete search history.

(56) References Cited

U.S. PATENT DOCUMENTS

| | | | |
|---|---|---|---|
| 4,820,740 A * | 4/1989 | Li | ............................ B01J 31/10 502/159 |
| 5,075,511 A | 12/1991 | Li | |
| 5,780,690 A | 7/1998 | Berg et al. | |
| 6,740,784 B2 | 5/2004 | Iwahara et al. | |
| 7,129,382 B2 * | 10/2006 | Iwahara | ................. C07C 37/20 568/728 |
| 2004/0127753 A1 | 4/2004 | Iwahara et al. | |
| 2004/0192975 A1 | 9/2004 | Iwahara et al. | |
| 2006/0211893 A1 | 9/2006 | Koga et al. | |

FOREIGN PATENT DOCUMENTS

| | | |
|---|---|---|
| EP | 1371623 A1 | 12/2003 |
| EP | 1415967 A1 | 5/2004 |
| EP | 1683779 A1 | 7/2006 |
| WO | 2012150554 A1 | 11/2012 |
| WO | 2012150559 A1 | 11/2012 |
| WO | 2012150560 A1 | 11/2012 |

OTHER PUBLICATIONS

Liu et al., "Effect of UV irradiation and physical aging on O2 and N2 transport properties of thin glassy poly(arylene ether ketone) copolymer films based on tetramethyl bisphenol A and 4,4'difluorobenzophenone," Polymer 87 (2016)202-214, available online Jan. 30, 2016. (Year: 2016).*
Researchgate, [online]; [retrieved on May 26, 2017] retrieved from the Internet https://www.researchgate.net/publication/263568415. Wang et al., "Bis (2-mercapto-ethyl) Amine Modification of Macroporous Sulfonic Resin Catalyst in Bisphenol-A Synthesis" AIChE Journal vol. 59 Issue 10, Oct. 2013, 9 pages.
Wang et al. "Condensation of Phenol and Acetone on a Modified Macroreticular Ion Exchange Resin Catalyst" Frontiers Chemical Science Engineer., 2013, pp. 218-225, vol. 7, Issue 2.

* cited by examiner

*Primary Examiner* — Pancham Bakshi
*Assistant Examiner* — Mark R Luderer
(74) *Attorney, Agent, or Firm* — Cantor Colburn LLP (57) ABSTRACT

In an embodiment, a method of producing a bisphenol comprises reacting a phenolic compound with a reactant comprising one or both of an aldehyde and a ketone in the presence of a catalyst system and methanol to produce the bisphenol; wherein the methanol is present in an amount of 250 to 5,000 ppm based on the total weight of the reactant; wherein the catalyst system comprises an ion-exchange resin comprising a plurality of sulfonic acid sites; and 5 to 35 mol % of an attached promoter molecule based on the total moles of the sulfonic acid sites in the catalyst system; and wherein the attached promoter molecule comprises at least two thiol groups per attached promoter molecule.

17 Claims, 2 Drawing Sheets

METHOD FOR PRODUCING A BISPHENOL

CROSS-REFERENCE TO

This application claims the benefit of European Patent Application Serial No. 16168830.4 filed May 10, 2016. The related application is incorporated herein in its entirety by reference.

TECHNICAL FIELD

The present disclosure relates to a method for producing a bisphenol.

BACKGROUND

Bisphenols such as Bisphenol A (BPA) (4,4'-(propane)-2,2-diyl)diphenol or p,p'-BPA) are often used in the production of plastics such as polycarbonates, polyesters, and epoxy resins. BPA is commercially produced by the condensation reaction of acetone and two equivalents of phenol in the presence of a catalyst such as an ion-exchange resin (IER). While ion-exchange resins in combination with an attached promotor have been shown to produce bisphenol A with a high purity, these ion-exchange resins often suffer from deactivation problems such as a rapid decrease in the reactivity and selectivity of the catalyst, even after relatively short production phases. This deactivation requires that the ion-exchange resin be either regenerated or even completely replaced, resulting in production stoppages and additional expenditure in maintaining the production plants.

An improved method for the production of bisphenols such as BPA using ion-exchange resin catalysts is therefore desirable.

BRIEF SUMMARY

Disclosed herein is a method for producing a bisphenol.

In an embodiment, A method of producing a bisphenol comprises reacting a phenolic compound with a reactant comprising one or both of an aldehyde and a ketone in the presence of a catalyst system and methanol to produce the bisphenol; wherein the methanol is present in an amount of 250 to 5,000 ppm based on the total weight of the reactant; wherein the catalyst system comprises an ion-exchange resin comprising a plurality of sulfonic acid sites; and 5 to 35 mol % of an attached promoter molecule based on the total moles of the sulfonic acid sites in the catalyst system; and wherein the attached promoter molecule comprises at least two thiol groups per attached promoter molecule.

In another embodiment, the use of a catalyst system for the manufacture of a bisphenol in the presence of 250 to 5,000 ppm methanol based on the total weight of the reactant; wherein the catalyst system comprises an ion-exchange resin comprising a plurality of sulfonic acid sites; wherein the catalyst system comprises 5 to 35 mol % of an attached promoter molecule based on the total moles of the sulfonic acid sites in the catalyst system; and wherein the attached promoter molecule comprises at least two thiol groups.

The above described and other features are exemplified by the following figures and detailed description.

BRIEF DESCRIPTION OF THE DRAWINGS

Refer now to the figures, which are exemplary embodiments, and wherein the like elements are numbered alike.

DETAILED DESCRIPTION

Bisphenols such as BPA can be produced by the condensation reaction of an aldehyde or ketone such as acetone and two equivalents of a phenolic compound catalyzed by a catalyst system, for example, comprising a crosslinked resin comprising a plurality of sulfonic acid sites. The presence of methanol in the acetone can disadvantageously result in a deactivation of the catalyst system as has been observed in a reduction in acetone conversion with reaction time. For example, U.S. Pat. No. 5,780,690 discloses first purifying their monophenols and carbonyl compounds prior to reacting to remove alkylating agents such as methanol to an amount of less than 0.01% relative to their weight as the presence of such agent results in an increased reduction of acetone conversion with time as compared to instances where the agent is not present.

A method of producing a bisphenol in the presence of methanol that could surprisingly result in an increased lifetime was discovered. The method comprises producing the bisphenol in the presence of a catalyst system and methanol; wherein the catalyst system comprises an ion-exchange resin comprising a plurality of sulfonic acid sites and 5 to 35 mole percent (mol %) of an attached promoter molecule based on the total moles of the sulfonic acid sites in the catalyst system; and wherein the attached promoter molecule comprises at least two thiol groups per promoter molecule. It was further surprisingly discovered that the catalyst system surprisingly showed a reduced deactivation as compared to a catalyst system where the attached promoter molecule comprised only a single thiol group per attached promoter molecule such as 2-mercaptoethylamine (also referred to as cysteamine) and where the catalyst system and the comparative catalyst system comprised the same amount of thiol groups in the respective catalyst systems.

The catalyst system can be formed by first preparing a crosslinked resin, sulfonating the crosslinked resin, and then functionalizing the sulfonated, crosslinked resin. The crosslinked resin can be formed by suspending a reaction mixture comprising a monovinyl aromatic monomer, a polyvinyl aromatic monomer, an initiator, and an optional aliphatic crosslinking monomer in an aqueous liquid to form a crosslinked copolymer. The monovinyl aromatic monomer can comprise styrene or a substituted styrene such as alpha-methyl styrene, vinyl toluene, ethyl vinyl benzene, vinyl naphthalene, and the like, or a combination comprising at least one of the foregoing can be used. The polyvinyl aromatic monomer can comprise divinyl benzene, divinyl toluene, trivinyl benzene, divinyl chloro benzene, diallyl phthalate, divinyl naphthalene, divinyl xylene, divinyl ethyl benzene, trivinyl naphthalene, polyvinyl anthracene, and the like, or a combination comprising at least one of the foregoing can be used. The polyvinyl aromatic monomer can comprise divinyl benzene. The aliphatic crosslinking monomer can comprise trivinyl cyclohexane, a di- or polyacrylate, and a di- or polymethacrylate, e.g., trimethylol propane trimethacrylate, ethylene glycol dimethacrylate, ethylene glycol diacrylate, neopentyl glycol dimethacrylate, a pentaerythritol tetra- or trimethacrylate, and the like, or a combination comprising at least one of the foregoing can be used.

The percentage of crosslinking of catalyst system formed by copolymerization of a monovinyl aromatic monomer and a polyvinyl aromatic monomer (such as sulfonated polystyrene-divinylbenzene copolymers) is based on the amount of crosslinker, i.e., polyvinyl aromatic monomer such as divinyl benzene and the optional aliphatic crosslinking monomer, present during manufacture of the catalyst. The polyvinyl aromatic monomer (VAM) can be present in an amount of less than or equal to 4 weight percent (wt %), 0.01 to 4 (0.01 wt %≤VAM≤4 wt %), or 0.1 to 2 wt %, or 0.5 to less than 2 wt % (0.5 wt %≤VAM<2 wt %), for example, 1.0 to 1.8 wt % (1.0 wt %≤VAM≤1.8 wt %), each based on the total weight of the monomers. The polyvinyl aromatic monomer can be present in an amount of 1.1 to 1.15 wt %, or 1.12 to 1.14 wt %, or 1.12 to 1.13 wt % each based on the total weight of the monomers. The foregoing amounts are particularly useful in the manufacture polystyrene-divinylbenzene copolymers.

The initiator can be a free radical initiator. Examples of free radical initiators include oil-soluble initiators such as benzoyl peroxide, lauroyl peroxide, t-butyl peroctoate, t-butyl peroxy benzoate, t-butyl peroxy pivalate, t-butylperoxy-2-ethylhexanoate, bis(4-t-butyl cyclohexyl) peroxy dicarbonate, azo compounds (such as azo bis(isobutrylonitrile), azobis(dimethyl valeronitrile), and the like), or a combination comprising one or more of the foregoing initiators can be used.

The reaction mixture can further comprise a stabilizer that stabilizes monomer droplets prior to polymerization. The stabilizer can comprise gelatin, starch, carboxymethylcellulose, poly(acrylic acid), poly(vinyl alcohol), a water-insoluble inorganic stabilizer in particulate form (such as bentonite, magnesium hydroxide, and the like), or a combination comprising one or more of the foregoing can be used.

The temperature of the reaction mixture can be increased to a polymerization temperature that is greater than or equal to activation temperature of the initiator in order to initiate the polymerization reaction. For example, the polymerization temperature can be 40 to 100 degrees Celsius (° C.), specifically, 50 to 90° C. The reaction can occur under agitation to produce a catalyst in the form of spherical beads. The spherical beads can have an average diameter of 20 micrometers to 1 millimeter (mm).

After polymerization, the crosslinked resin can be separated from the suspending medium (for example, by gravity, centrifugal flow, hydraulic separation, or filtration), dried, sulfonated, and functionalized.

The crosslinked resin can then be is sulfonated with a sulfonating reagent composition and optionally a sulfone crosslinker to form sulfonic acid sites on the crosslinked resin. The sulfonating reagent composition can comprise chlorosulfonic acid, sulfur trioxide, sulfuric acid, or a combination comprising one or more of the foregoing. The sulfonating reagent composition can further comprise a boron compound such as boric acid and boron oxide. The sulfonating reagent composition can comprise, for example, a sulfuric acid/SO$_3$ mixture having an acid concentration of 101 to 104.5% in order to introduce an average of at least one sulfonic acid group per aromatic nucleus.

Exemplary ion exchange resins can include, but are not limited to, DIAION™SK104, DIAION™SK1B, DIAION™PK208, DIAION™PK212 and DIAION™PK216 (manufactured by Mitsubishi Chemical Industries, Limited), A-121, A-232, and A-131, (manufactured by Rohm & Haas), LEWATIT™K1131, LEWATIT™K1221 (manufactured by LANXESS), DOWEX™50W2X, DOWEX™50 W4X, DOWEX™50W8X resins (manufactured by DOW CHEMICAL), and PUROLITE™CT222 and PUROLITE™CT122 (manufactured by Purolite).

The sulfonated, crosslinked resin can then be functionalized with a promoter molecule that comprises at least two thiol groups, for example, 2 to 6, or 2 to 4 thiol groups. The sulfonated, crosslinked resin can further be optionally functionalized with a promoter molecule that comprises one thiol group. The sulfonated, crosslinked resin can then be functionalized such that the resultant catalyst system comprises 5 to 35 mol %, or 10 to 30 mol %, 10 to 25 mol %, or 15 to 25 mol % of an attached promoter molecule based on the total moles of the sulfonic acid sites in the catalyst system. The sulfonated, crosslinked resin can then be functionalized such that the resultant catalyst system comprises 10 to 20 mol % of an attached promoter molecule based on the total moles of the sulfonic acid sites in the catalyst system.

The attached promoter molecule can have the formula:

wherein a and b are each independently an integer of 0 to 5, $R_n$ can be an amine, a pyridine, a phosphonium, a $C_{1-4}$ group and the like; and $R_1$, $R_2$, $R_3$, and $R_4$ can each independently be H, OH, SH, or an alkyl group.

The catalyst system can have the formula:

wherein IER is the crosslinked resin; a, b, $R_1$, $R_2$, $R_3$, and $R_4$ are defined above; and $R_n$ is covalently or ionically bound to the sulfonic acid site and can be an amine, a pyridine, a phosphonium, a $C_{1-4}$ group and the like. For example, R″ can be an amine and $R_1$, $R_2$, $R_3$, and $R_4$ can each be H.

The catalyst system can be used as a fixed-bed catalyst in condensation reactions, for example, the condensation of a phenolic compound with a reactant comprising one or both of a ketone and an aldehyde to produce bisphenols. The catalyst system can be exposed to a feed comprising a condensation mixture comprising the phenolic compound and a reactant comprising one or both of a ketone and an aldehyde. The feed can comprise less than or equal to 2 wt %, or 0 to 2 wt %, or 0 to 1 wt % of water based on the total weight of the feed. The feed can comprise methanol in an amount of 250 to 5,000 parts per million by weight (ppm), or 250 to 4,000 ppm, or 260 to 3,000 ppm, or 260 to 2,000 ppm based on the total weight of the reactant. The methanol present in the feed can be present during the reaction. In other words, a reactant stream or the feed can be an unpurified stream that does not undergo a methanol purification step.

The reaction of the phenolic compound and the aldehyde or ketone can occur in a stoichiometric amount or in a molar excess of the phenolic compound. For example, the molar ratio of the phenolic compound to the aldehyde or ketone can be 20:1 to 2:1. The feed can comprise 3 to 15 wt %, or 5 to 10 wt % of the reactant based on the total weight of the feed.

The reaction can occur at a temperature of 40 to 150° C., or 55 to 100° C. with, for example, 1 to 40 wt % catalyst based on the weight of the phenolic compound and the aldehyde or ketone. The reaction can occur at a weight hourly space velocity (WHSV) of 0.2 to 30 inverse hours ($hr^{-1}$), or 0.5 to 20 $hr^{-1}$.

The catalyst system can be particularly useful in large commercial reactors used to produce high volumes of bisphenols such as BPA. Due to the large size of fixed bed bisphenol reactors and the viscosity of the bisphenol reaction stream, bisphenol production rates are sensitive to pressure drops that occur across the reactor. Pressure drops can be affected by catalyst particle size and particle uniformity, but also particle compressibility. The catalyst system can have an average particle size of the catalyst is 300 to 1,500 micrometers, or 300 to 1,000 micrometers, or 350 to 500 micrometers at a moisture content of 60 to 90 wt %. For down-flow operation, the catalyst system can have an average particle size of 600 to 1,500 micrometers at a moisture content of 60 to 90 wt %.

The catalyst system can have an improved lifetime as compared to a corresponding cysteamine catalyst system. For example, the catalyst system disclosed herein can have an improved lifetime, for example, the catalyst system can have a lifetime improvement of greater than or equal to 25%, or greater than or equal to 40%, or as much as 45% as compared to a corresponding cysteamine catalyst system having the same level of acid site neutralization. The catalyst system can have an improved lifetime, for example, an improvement of greater than or equal to 25%, greater than or equal to 100%, or even greater than or equal to 140% as compared to a corresponding cysteamine catalyst system having the same concentration of thiol groups. This improvement can be seen, for example, over the methanol concentration of 250 to 5,000 ppm based on the total weight of the reactant. The lifetime can be determined experimentally based on a time when the concentration of p,p-BPA in the effluent is 10 wt %; or can be determined using a best fit line from experimental data of p,p-BPA with time and calculating the time at which the concentration is expected to be 10 wt %.

The ketone can have the formula $R^{k1}$—(C=O)—$R^{k2}$, wherein $R^{k1}$ and $R^{k2}$ can each independently be a $C_{1-18}$, specifically, $C_{1-6}$ aliphatic group, and can further comprise heteroatoms such as one or more of halogens, oxygen, nitrogen, sulfur, silicon, and phosphorous provided that such substituents do not substantially adversely affect the reaction or reaction product. $R^{k1}$ and $R^{k2}$ can together form a $C_{5-18}$ cycloalkyl group (such as cyclohexanone or methylcyclohexanone) or a $C_{5-18}$ cycloalkylene group. The aldehyde can have the formula $R^{k1}$—(C=O)—H, wherein $R^{k1}$ can be that described above or hydrogen.

A wide variety of phenolic compounds can be used, which, as used herein means an aromatic compound substituted with a single hydroxyl group. The aromatic compound can be monocyclic or polycyclic, and can be substituted with up to 5 substituents, provided that such substituents do not substantially adversely affect the reaction or reaction product.

The method can result in the formation of a bisphenol of the formula HO—$R^1$—OH, wherein the $R^1$ group can contain an aliphatic, an alicyclic, or an aromatic moiety. For example, the bisphenol can have the formula (2)

HO-$A^1$-$Y^1$-$A^2$-OH (2)

wherein each of $A^1$ and $A^2$ is a monocyclic divalent aromatic group and $Y^1$ is a single bond or a bridging group having one or more atoms that separate $A^1$ from $A^2$. One atom can separate $A^1$ from $A^2$.

The bisphenol can have the formula (3)

(3)

wherein $R^a$ and $R^b$ are each independently a halogen, $C_{1-12}$ alkoxy, or $C_{1-12}$ alkyl; and p and q are each independently integers of 0 to 4. It will be understood that $R^a$ is hydrogen when p is 0, and likewise $R^b$ is hydrogen when q is 0. Also in formula (3), $X^a$ is a bridging group connecting the two hydroxy-substituted aromatic groups, where the bridging group and the hydroxy substituent of each $C_6$ arylene group are disposed ortho, meta, or para (specifically, para) to each other on the $C_6$ arylene group. The bridging group $X^a$ can be single bond, —O—, —S—, —S(O)—, —S(O)$_2$—, —C(O)—, or a $C_{1-18}$ organic group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. p and q can each be 1, and $R^a$ and $R^b$ are each a $C_{1-3}$ alkyl group, specifically, methyl, disposed meta to the hydroxy group on each arylene group.

$X^a$ can be a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene.

$X^a$ can be a $C_{1-18}$ alkylene group, a $C_{3-18}$ cycloalkylene group, a fused $C_{6-18}$ cycloalkylene group, or a group of the formula —$B^1$-G-$B^2$— wherein $B^1$ and $B^2$ are the same or different $C_{1-6}$ alkylene group and G is a $C_{3-12}$ cycloalkylidene group or a $C_{6-16}$ arylene group. For example, $X^a$ can be a substituted $C_{3-18}$ cycloalkylidene of formula (4)

(4)

wherein $R^r$, $R^p$, $R^q$, and $R^t$ are each independently hydrogen, halogen, oxygen, or $C_{1-12}$ hydrocarbon groups; Q is a direct bond, a carbon, or a divalent oxygen, sulfur, or —N(Z)— where Z is hydrogen, halogen, hydroxy, $C_{1-12}$ alkyl, $C_{1-12}$ alkoxy, or $C_{1-12}$ acyl; r is 0 to 2, t is 1 or 2, q is 0 or 1, and k is 0 to 3, with the proviso that at least two of $R^r$, $R^p$, $R^q$, and $R^t$ taken together are a fused cycloaliphatic, aromatic, or heteroaromatic ring. It will be understood that where the fused ring is aromatic, the ring as shown in formula (4) will have an unsaturated carbon-carbon linkage where the ring is fused. When k is one and q is 0, the ring as shown in formula (4) contains 4 carbon atoms, when k is 2, the ring as shown in formula (4) contains 5 carbon atoms, and when k is 3, the ring contains 6 carbon atoms. Two adjacent groups (e.g., $R^q$ and $R^t$ taken together) can form an aromatic group or $R^q$ and $R^t$ taken together can form one aromatic group and $R^r$ and $R^p$ taken together form a second aromatic group. When $R^q$ and $R^t$ taken together form an aromatic group, $R^p$ can be a double-bonded oxygen atom, i.e., a ketone.

Specific examples of bisphenol compounds of formula (3) include 1,1-bis(4-hydroxyphenyl) methane, 1,1-bis(4-hydroxyphenyl) ethane, 2,2-bis(4-hydroxyphenyl) propane (hereinafter "bisphenol A" or "BPA"), 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-2-methylphenyl) propane, 1,1-bis(4-hydroxy-t-butylphenyl) propane, 3,3-bis(4-hydroxyphenyl) phthalimidine, 2-phenyl-3,3-bis(4-hydroxyphenyl) phthalimidine (PPPBP), and 1,1-bis(4-hydroxy-3-methylphenyl)cyclohexane (DMBPC). Combinations comprising at least one of the foregoing dihydroxy compounds can also be used. The polycarbonate can be a linear homopolymer derived from bisphenol A, in which each of $A^1$ and $A^2$ can be p-phenylene, and $Y^1$ can be isopropylidene in formula (3).

The catalyst system can be used in the condensation of cyclohexanone and o-cresol to produce 1,1-bis(4-hydroxy-3-methylphenyl) cyclohexane (DMBPC).

The catalyst system can be used in the condensation of acetone and phenol to produce BPA.

After formation of the bisphenol, the product mixture can be post-treated to purify the bisphenol. The post-treatment can comprise crystallization of bisphenol to form crystals comprising a crystallized bisphenol and/or a crystallized bisphenol adduct. The crystallization can comprise a vacuum cooling step. The crystallization can be facilitated by adding water, for example, in an amount of less than or equal to 3 wt %, specifically, 0.1 to 3 wt % based on the total weight of the product mixture. The crystals can be optionally separated, for example, by filtration and melted in a melting unit. If the melt comprises sulfur, then a base (such as sodium hydroxide and potassium hydroxide) can be added to the melt to form a melt stream with a reduced sulfur content. The melted stream can be filtered, further purified, and then solidified, for example, in a flaking unit.

The bisphenols produced by this process can be used to manufacture a polycarbonate. A "polycarbonate" as used herein means compositions having repeating structural carbonate units of formula (1)

(1)

in which the $R^1$ groups contain aliphatic, alicyclic, and/or aromatic moieties (e.g., greater than or equal to 30 percent, specifically, greater than or equal to 60 percent, of the total number of $R^1$ groups can contain aromatic moieties and the balance thereof are aliphatic, alicyclic, or aromatic). Optionally, each $R^1$ can be a $C_{6-30}$ aromatic group, that is, can contain at least one aromatic moiety. $R^1$ can be derived from the bisphenol.

The following non-limiting examples further illustrate the various embodiments described herein.

EXAMPLES

In the examples, the concentrations of p,p-BPA and o,p-BPA were determined by high performance liquid chromatography (HPLC) taken at the effluent of the reactor.

Examples 1-4

Catalyst Preparation

Sulfonated polystyrene catalysts crosslinked with 2% divinylbenzene were modified in-situ with a promoter molecule of bis-2-(mercaptoethyl)amine (BMEA) (Catalysts 1-3) or cysteamine (Catalyst 4) and are shown in Table 1, where the mole percent of the promoter molecule is based on the total moles of the sulfonic acid sites to be neutralized in the catalyst system. Specifically, the catalysts were prepared by dissolving the amount of BMEA or cysteamine shown in Table 1 in 40 grams (g) of demineralized water. Once the BMEA or cysteamine were dissolved, 10 g of the cross-linked sulfonated ion exchange resin and 40 g of demineralized water were added. The pH of the solution was adjusted to a value of 3. The solution was then heated to 80° C. for 7 hours (hr) under nitrogen. Afterwards, the catalyst was washed several times with absolute ethanol, washed several times with demineralized water, and then dried under vacuum.

TABLE 1

| Catalyst | Example | | | |
| --- | --- | --- | --- | --- |
| | 1 | 2 | 3 | 4 |
| Attached promoter molecule | BMEA | BMEA | BMEA | Cysteamine |
| Acid site neutralization level (mol %) | 10 | 20 | 30 | 20 |

Example 5

Batch Preparation of BPA

The performance of Catalysts 1-4 was tested in a batch reactor by reacting a solution of 4 wt % acetone in phenol in the presence of 1 g of the respective catalyst. The reaction proceeded for 6 hours at 70° C. The formation of p,p-BPA and the ratio of p,p-BPA to o,p-BPA were monitored with time and are shown in FIG. 1 and FIG. 2, respectively.

Figure 1:
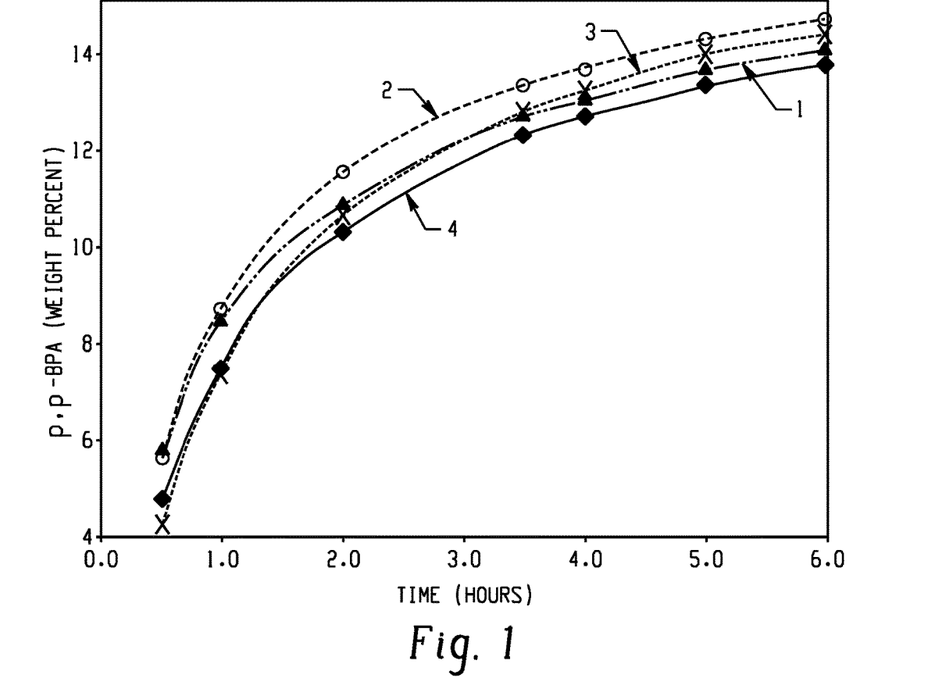
FIG. 1 is a graphical illustration of the bisphenol A production in batch mode with time for Catalysts 1-4.
Figure 2:
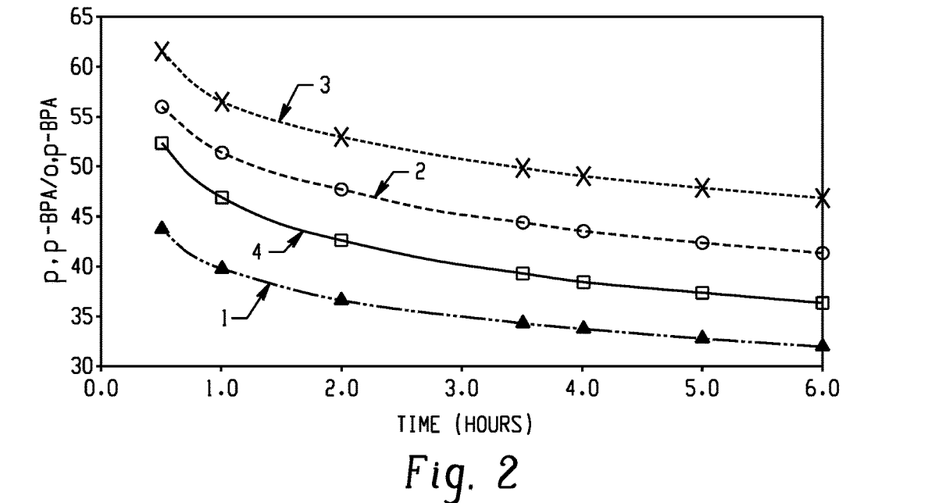
FIG. 2 is a graphical illustration of the p,p/o,p (para-para/ortho,para) ratio in batch mode with time for Catalysts 1-4.

FIG. 1 shows that for all of the catalyst systems of Catalysts 1-3, the BPA production was higher as compared to the cysteamine catalyst system of Catalyst 4. FIG. 2 shows that the p,p/o,p ratio is greater for the Catalysts 2 and 3 having greater than 10 wt % of acid sites neutralized in the final catalyst as compared to the cysteamine catalyst system of Catalyst 4. Without being bound by theory, it is believed that catalyst performance is determined by the balance between reactive acid sites and amount of promoter attached to the catalyst.

Examples 6-12

Continuous Preparation of BPA

The performance of Catalysts 1, 2, and 4 was tested in a continuous reactor comprising 2 reactors arranged in parallel, where 6.25 g the respective dry catalyst was located in a fixed bed in each reactor. A feed comprising 6 wt % acetone in phenol was continuously fed to the reactor at a WHSV of 8 hr$^{-1}$ and the reactions were carried out at 75° C. Examples 6-12 were run for at least 300 hours with varying methanol concentrations, based on the total weight of the feed, as shown in Table 2.

Figure 3:
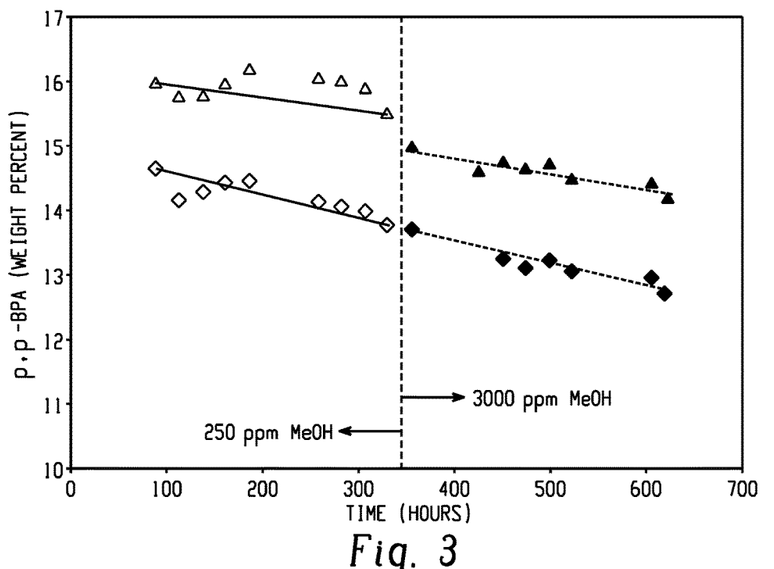
FIG. 3 is a graphical illustration of the bisphenol A production in continuous mode with time for Examples 6, 7, 10 and 12.
Figure 4:
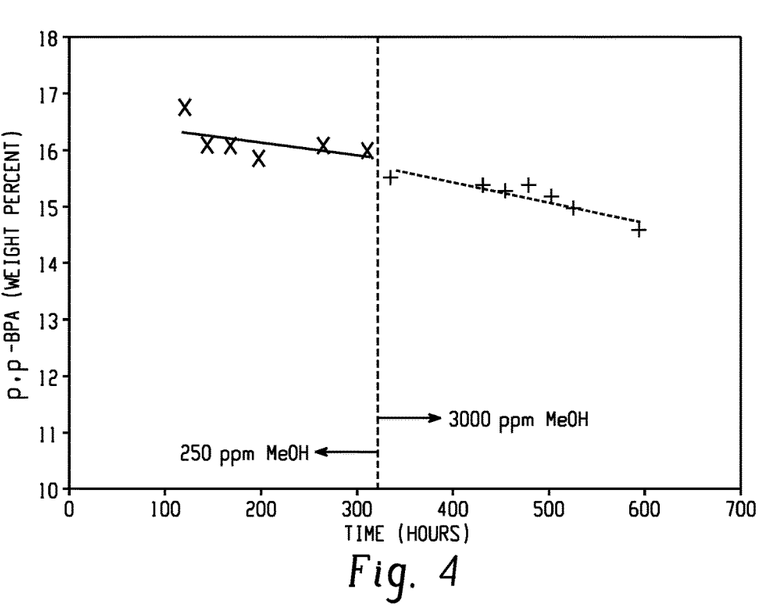
FIG. 4 is a graphical illustration of the bisphenol A production in continuous mode with time for Examples 8 and 9.

Examples 6 and 10 were run for at least another 300 hours, whereafter the first 300 hours (at time, t, shown in FIG. 3 and FIG. 4 by the dashed line), the methanol concentration in the feed was increased to 3,000 ppm based on the total weight of the feed, Examples 7 and 12. The p,p-BPA production with time for Examples 6, 7, 10, and 12 are shown in FIG. 3, where the open triangles represent the data of Example 6 and where the best fit line has a formula of y=−0.0013x+16.148, the closed triangles represent the data of Example 7 and where the best fit line has a formula of y=−0.0016x+15.499, the "Xs" represent the data of Example 10 and where the best fit line has a formula of y=−0.0024x+14.719, and the plusses represent the data of Example 12 and where the best fit line has a formula of y=−0.0034x+14.926. The p,p-BPA production with time for Examples 8 and 9 are shown in FIG. 4 where the open diamonds represent the data of Example 8 and where the best fit line has a formula of y=−0.0023x+16.624; and the closed diamonds represent the data of Example 9 and where the best fit line has a formula of y=−0.0034x+16.835.

The acetone conversion, selectivity and the reduction in p,p-BPA produced after 300 hours of continuous operation is shown in Table 2. The acetone conversion was estimated from the HPLC component analysis of the reactor effluent. The acetone conversion and the selectivity were determined using the following equations:

$$\text{Acetone conversion (\%)} = \frac{\text{reaction product in the effluent (wt \%)}}{\text{acetone in the feed (wt \%)}} \times 100$$

$$\text{Selectivity (\%)} = \frac{p, pBPA \text{ (wt \%)}}{\text{reaction product in the effluent (wt \%)}} \times 100$$

In Table 2, the reduction in p,p-BPA formation was used to determine the impact of the methanol concentration after 300 hours (t=300 hours) of continuous operation and was determined using the following equation:

$$BPA \text{ reduction (wt \%)}_{t=0\ hr} = \frac{p, pBPA_{t=0\ hr} - p, pBPA_{t=300\ hr}}{p, pBPA_{t=0\ hr}} \times 100$$

TABLE 2

| | Example | | | | | | |
|---|---|---|---|---|---|---|---|
| | 6 | 7 | 8 | 9 | 10 | 11 | 12 |
| Catalyst | 1 | 1 | 2 | 2 | 4 | 4 | 4 |
| MeOH concentration (mg MeOH/kg acetone) | 250 | 3,000 | 250 | 3,000 | 250 | 700 | 3,000 |
| Acetone conversion (%) after 300 hours | 73.0 | 68.2 | 74.1 | 68.0 | 69.1 | 59.3 | 59.5 |
| Selectivity (%) | 93.3 | 93.2 | 93.7 | 94.1 | 93.7 | 93.7 | 93.8 |
| p, p-BPA reduction (wt %) after 300 hours | <3 | 11.5 | 5.5 | 13.1 | 11.5 | 19.2 | 33.9 |
| Estimated lifetime (hr) (hours producing p,p-BPA until y = 10 wt %) | 4,729 | 3,437 | 2,880 | 2,010 | 1,966 | — | 1,449 |
| BPA production after 300 hours (p, p-BPA/catalyst) | 405 | 311 | 399 | 302 | 384 | — | 290 |

Table 2 shows that Examples 6-9 all had increased acetone conversions as compared to Examples 10-12 using the cysteamine catalyst system. Table 2 further shows that the reduction in BPA formation after 300 hours is less for the catalyst systems as compared to the cysteamine catalyst systems. For example, Example 8 shows a reduction of BPA formation of only 5.5 wt % as compared to Example 10 having a reduction of BPA formation of 11.5 wt %. Likewise, Example 9 shows a reduction of BPA formation of only 13.1 wt % as compared to Example 12 having a reduction in BPA formation of 33.9 wt %.

FIG. 3 shows that over all times, the reaction of Examples 6 and 7 produce more BPA than that of Examples 10 and 12. Further, the slope of the equations shown in FIG. 3 show that the catalyst system has an increased lifetime with more p,p-BPA production than the cysteamine catalyst system. For example, Catalyst 1 of Example 6 contains same amount of thiol groups as Catalyst 4 of Example 10, but displays a 140% increase in lifetime as compared to Example 10. The lifetime analysis is based on the catalyst maintaining a levels of greater than or equal to 10 wt % p,p-BPA in the effluent of the reactor.

Similarly, FIG. 4 shows that, over all times, the reaction of Examples 8 and 9 produce more BPA than that of Examples 10 and 12. Further, the slopes of the equations shown in FIG. 4 show that the catalyst system has an increased lifetime with more p,p-BPA production than the cysteamine catalyst system. For example, Catalyst 2 of Example 8 contains the same amount of acid sites as Catalyst 4 of Example 10, but displays a 46% increase in lifetime as compared to Example 10. The lifetime analysis is based on the catalyst maintaining a levels of greater than or equal to 10 wt % p,p-BPA in the effluent of the reactor.

Set forth below are non-limiting embodiments of the present method of making a bisphenol.

Embodiment 1: A method of producing a bisphenol comprising: reacting a phenolic compound with a reactant comprising one or both of an aldehyde and a ketone in the presence of a catalyst system and methanol to produce the bisphenol; wherein the methanol is present in an amount of 250 to 5,000 ppm based on the total weight of the reactant; wherein the catalyst system comprises an ion-exchange resin comprising a plurality of sulfonic acid sites; and 5 to 35 mol % of an attached promoter molecule based on the total moles of the sulfonic acid sites in the catalyst system; and wherein the attached promoter molecule comprises at least two thiol groups per attached promoter molecule.

Embodiment 2: The method of Embodiment 1, wherein the catalyst system comprises 10 to 30 mol %, of the attached promoter molecule based on the total moles of the sulfonic acid sites in the catalyst system.

Embodiment 3: The method of any one of the preceding embodiments, wherein the catalyst system comprises 10 to 25 mol % of the attached promoter molecule based on the total moles of the sulfonic acid sites in the catalyst system.

Embodiment 4: The method of any one of the preceding embodiments, wherein the catalyst system comprises 10 to 20 mol % of the attached promoter molecule based on the total moles of the sulfonic acid sites in the catalyst system.

Embodiment 5: The method of any one of the preceding embodiments, wherein the catalyst system is a reaction product of a monovinylaromatic monomer and less than or equal to 4 wt % of a polyvinyl aromatic monomer based on the total amount of monomer.

Embodiment 6: The method of Embodiment 3, wherein the monovinylaromatic monomer comprises styrene and/or wherein the polyvinyl aromatic monomer comprises divinyl benzene.

Embodiment 7: The method of any one of Embodiments 3-4, wherein the catalyst system is the polymerization product of 1.0 to 2.0 wt %, or greater than 1.0 to 1.5 wt %, or greater than 1.0 to 1.2 wt %, or greater than 1.0 to 1.25 wt %, or greater than 1.1 to 1.15 wt %, or 1.12 to 1.14 wt % of the polyvinyl aromatic monomer.

Embodiment 8: The method of any one of the preceding embodiments, wherein the catalyst system has the formula wherein IER is the crosslinked resin, a and b are each independently an integer of 0 to 5, $R_n$ is covalently or ionically bound to the sulfonic acid site and is an amine, a pyridine, a phosphonium, or a $C_{1-4}$ group; and $R_1$, $R_2$, $R_3$, and $R_4$ are each independently H, OH, SH, or an alkyl group.

Embodiment 9: The method of any one of the preceding embodiments, wherein the attached promoter molecule has the formula wherein a and b are each independently an integer of 0 to 5, $R_n$ is an amine, a pyridine, a phosphonium, or a $C_{1-4}$ group; and $R_1$, $R_2$, $R_3$, and $R_4$ are each independently H, OH, SH, or an alkyl group.

Embodiment 10: The method of any one of the preceding embodiments, wherein the attached promoter molecule comprises bis-2-(mercaptoethyl)amine.

Embodiment 11: The method of any one of the preceding embodiments, wherein an average particle size of the catalyst is 300 to 1,500 micrometers at a moisture content of 60 to 90 wt %.

Embodiment 12: The method of any one of the preceding embodiments, wherein the phenolic compound comprises at least one of a monocyclic phenolic compound and a polycyclic phenolic compound; and wherein the monocyclic phenolic compound and/or the polycyclic phenolic compound is optionally substituted with up to 5 substituents.

Embodiment 13: The method of any one of the preceding embodiments, wherein the phenolic compound comprises phenol, the reactant comprises acetone.

Embodiment 14: The method of any one of the preceding embodiments, wherein the catalyst system has an increased lifetime as compared to a cysteamine catalyst system comprising an attached cysteamine promoter; wherein the cysteamine catalyst system has one of a same amount of an acid site neutralization of the respective sulfonic acid sites or a same concentration of thiol groups as the catalyst system.

Embodiment 15: Use of a catalyst system, preferably the catalyst system of any one of the preceding claims, for the manufacture of a bisphenol in the presence of 250 to 5,000 ppm methanol based on the total weight of the reactant; wherein the catalyst system comprises an ion-exchange resin comprising a plurality of sulfonic acid sites; wherein the catalyst system comprises 5 to 35 mol % of an attached promoter molecule based on the total moles of the sulfonic acid sites in the catalyst system; and wherein the attached promoter molecule comprises at least two thiol groups.

The terms "a" and "an" do not denote a limitation of quantity, but rather denote the presence of at least one of the referenced item. The term "or" means "and/or" unless clearly indicated otherwise by context. "Optional" or "optionally" means that the subsequently described event or circumstance may or may not occur, and that the description includes instances where the event occurs and instances where it does not. The endpoints of all ranges directed to the same component or property are inclusive of the endpoints, are independently combinable, and include all intermediate points and ranges. For example, ranges of "up to 25 wt %, or 5 to 20 wt %" is inclusive of the endpoints and all intermediate values of the ranges of "5 to 25 wt %," such as 10 to 23 wt %, etc.). The term "combination" is inclusive of blends, mixtures, reaction products, and the like.

Unless defined otherwise, technical and scientific terms used herein have the same meaning as is commonly understood by one of skill in the art to which this disclosure belongs.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

Reference throughout the specification to "an embodiment", "another embodiment", "some embodiments", and so forth, means that a particular element (e.g., feature, structure, step, or characteristic) described in connection with the embodiment is included in at least one embodiment described herein, and may or may not be present in other embodiments. In addition, it is to be understood that the described elements may be combined in any suitable manner in the various embodiments.

In general, the compositions, methods, and articles can alternatively comprise, consist of, or consist essentially of, any ingredients, steps, or components herein disclosed. The compositions, methods, and articles can additionally, or alternatively, be formulated, conducted, or manufactured so as to be devoid, or substantially free, of any ingredients, steps, or components not necessary to the achievement of the function or objectives of the present claims.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

We claim:

1. A method of producing a bisphenol comprising:
reacting a phenolic compound with a reactant comprising one or both of an aldehyde and a ketone in the presence of a catalyst system and methanol to produce the bisphenol; wherein the methanol is present in an amount of 250 to 5,000 ppm based on the total weight of the reactant;
wherein the catalyst system comprises an ion-exchange resin comprising a plurality of sulfonic acid sites; and 5 to 35 mol % of an attached promoter molecule based on the total moles of the sulfonic acid sites in the catalyst system; and wherein the attached promoter molecule comprises at least two thiol groups per attached promoter molecule;
wherein an average particle size of the catalyst system is 300 to 1,500 micrometers at a moisture content of 60 to 90 wt %.

2. The method of claim 1, wherein the catalyst system comprises 10 to 30 mol %, of the attached promoter molecule based on the total moles of the sulfonic acid sites in the catalyst system.

3. The method of claim 1, wherein the catalyst system comprises 10 to 25 mol % of the attached promoter molecule based on the total moles of the sulfonic acid sites in the catalyst system.

4. The method of claim 1, wherein the catalyst system comprises 10 to 20 mol % of the attached promoter molecule based on the total moles of the sulfonic acid sites in the catalyst system.

5. The method of claim 1, wherein the catalyst system is a reaction product of a monovinylaromatic monomer and less than or equal to 4 wt % of a polyvinyl aromatic monomer based on the total amount of monomer.

6. The method of claim 5, wherein the monovinylaromatic monomer comprises styrene.

7. The method of claim 5, wherein the polyvinyl aromatic monomer comprises divinyl benzene.

8. The method of claim 1, wherein the catalyst system is the polymerization product of 1.0 to 2.0 wt % of the polyvinyl aromatic monomer.

9. The method of claim 1, wherein the catalyst system has the formula wherein IER is a crosslinked resin, a and b are each independently an integer of 0 to 5, $R_n$ is covalently or ionically bound to the sulfonic acid site and is an amine, a pyridine, a phosphonium, or a $C_{1-4}$ group; and $R_1$, $R_2$, $R_3$, and $R_4$ are each independently H, OH, SH, or an alkyl group.

10. The method of claim 1, wherein the attached promoter molecule has the formula wherein a and b are each independently an integer of 0 to 5, $R_n$ is an amine, a pyridine, a phosphonium, or a $C_{1-4}$ group; and $R_1$, $R_2$, $R_3$, and $R_4$ are each independently H, OH, SH, or an alkyl group.

11. The method of claim 1, wherein the attached promoter molecule comprises bis-2-(mercaptoethyl)amine.

12. The method of claim 1, wherein the phenolic compound comprises a monocyclic phenolic compound.

13. The method of claim 12, wherein the monocyclic phenolic compound is substituted with up to 5 substituents.

14. The method of claim 1, wherein the phenolic compound comprises phenol, the reactant comprises acetone.

15. The method of claim 1, wherein the catalyst system has an increased lifetime as compared to a cysteamine catalyst system comprising an attached cysteamine promoter; wherein the cysteamine catalyst system has one of a same amount of an acid site neutralization of the respective sulfonic acid sites or a same concentration of thiol groups as the catalyst system.

16. The method of claim 1, wherein the phenolic compound comprises a polycyclic phenolic compound.

17. The method of claim 16, wherein the polycyclic phenolic compound is substituted with up to 5 substituents.

\* \* \* \* \*